(12) United States Patent
Texier-Nogues et al.

(10) Patent No.: US 8,513,394 B2
(45) Date of Patent: Aug. 20, 2013

(54) SACCHARIDE FLUORESCENT SUBSTRATES, PREPARATION METHOD AND USES THEREOF

(75) Inventors: Isabelle Texier-Nogues, Grenoble (FR); Véronique Robert, Grenoble (FR); Jean-Luc Coll, Claix (FR); Anne Imberty, Claix (FR)

(73) Assignees: Commissariat a l'Energie Atomique, Paris (FR); Institut National de la Sante et de la Recherche Medicale (Inserm), Paris (FR); Centre National de la Recherche Scientifique, Paris (FR)

( * ) Notice: Subject to any disclaimer, the term of this patent is extended or adjusted under 35 U.S.C. 154(b) by 1120 days.

(21) Appl. No.: 11/996,084

(22) PCT Filed: Jul. 21, 2006

(86) PCT No.: PCT/FR2006/001786
§ 371 (c)(1),
(2), (4) Date: Jul. 28, 2008

(87) PCT Pub. No.: WO2007/010145
PCT Pub. Date: Jan. 25, 2007

(65) Prior Publication Data
US 2008/0299044 A1   Dec. 4, 2008

(30) Foreign Application Priority Data

Jul. 21, 2005   (FR) ..................... 05 07759

(51) Int. Cl.
| | | |
|---|---|---|
| *C07H 15/00* | (2006.01) | |
| *C07H 15/18* | (2006.01) | |
| *C12Q 1/34* | (2006.01) | |
| *G01N 21/64* | (2006.01) | |

(52) U.S. Cl.
CPC .............. *C07H 15/00* (2013.01); *C07H 15/18* (2013.01); *G01N 21/6428* (2013.01)
USPC ............. 536/4.1; 536/18.1; 436/172; 435/14; 435/18

(58) Field of Classification Search
None
See application file for complete search history.

(56) References Cited

U.S. PATENT DOCUMENTS

| | | | |
|---|---|---|---|
| 2004/0053287 A1 | 3/2004 | Lawler, Jr. | |
| 2005/0064471 A1 * | 3/2005 | Griffey et al. | ..... 435/6 |
| 2005/0250134 A1 * | 11/2005 | Sheng et al. | ..... 435/6 |

FOREIGN PATENT DOCUMENTS

EP   0 731 178   9/1996

OTHER PUBLICATIONS

Platteeuw et al., "Use of the *Escherichia coli*13-Glucuronidase (GusA) Gene as a Reporter Gene for Analyzing Promoters in Lactic Acid Bacteria" Applied and Environmental Microbiology (1994) pp. 587-593.*

S. Cottaz et al: "A Fluorescence-Quenched Chitopentaose for the Study of Endo-Chitinases and Chitobiosidases." European Journal of Biochemistry, vol. 267, pp. 5593-5600, XP 002377041, 2000.

K. Matsuoka et al: "A Bi-Fluorescence-Labeled Substrate for Ceramide Glycanase Based on Fluorescence Energy Transfer", Carbohydrate Research, vol. 276, pp. 31-42, XP 004021862, 1995.

E. Giorgio et al: "Theoretical Simulation of the Electronic Circular Dichroism Spectrum of Calicheamicin", Bioorganic & Medical Chemistry, vol. 13, pp. 5072-5079, XP 005045017, 2005.

M. Takeuchi et al: "Sugar Building-Block As a Fine-Tunable Link for Electron-Donor-Electron-Acceptor Couples", Tetrahedron Letters, vol. 40, pp. 3745-3748, XP 004163821, 1999.

\* cited by examiner

*Primary Examiner* — Eric S Olson
(74) *Attorney, Agent, or Firm* — Oblon, Spivak, McClelland, Maier & Neustadt, L.L.P.

(57) ABSTRACT

A fluorescent enzymatic substrate including a backbone saccharide nature having at least one saccharide unit. The saccharide unit includes a fluorophore $F_1$ and an inhibitor $I_1$ of the fluorescence of $F_1$. The fluorophore $F_1$ and the inhibitor $I_1$, either directly or by the spacer arms $B_1$ and $B_2$, respectively, when at least one $B_1$ and $B_2$ is present, are grafted on the same saccharide unit of the backbone saccharide. One of th groups is $F_1$ and $I_1$ grafted in the anomeric position 1 of the saccharide unit.

22 Claims, 3 Drawing Sheets

SACCHARIDE FLUORESCENT SUBSTRATES, PREPARATION METHOD AND USES THEREOF

The present invention relates to fluorescent enzymatic substrates of saccharide nature comprising, on the same saccharide unit, a fluorophore $F_1$ and an inhibitor of the fluorescence of $F_1$, to their use for preparing a diagnostic reagent for in vivo functional imaging, and also to the diagnostic reagent for functional imaging containing at least such an enzymatic substrate.

Fluorescence is a widely used technique for detecting enzymatic activities in vitro. It is a relatively inexpensive, rapid and generally very sensitive technique.

Many enzymes of significant biological importance have saccharide derivatives as substrates. In fact, reporter genes expressing various enzymes, such as β-galactosidase (β-gal), β-glucuronidase (β-glu), chloramphenicol, acetyltransferase or luciferase, or fluorescent proteins such as green fluorescent protein (GFP), are widely used today in biology for studying gene expression (transcription and translation of DNA to proteins), transfection, or other biological processes. Reporter genes can serve as controls for demonstrating the introduction and the transcription of another gene of interest, located on the same coding portion of the DNA. DNA constructs containing the reporter genes are introduced into animals so as to form transgenic animals. For example, the number of transgenic mice already constructed is very high and is rapidly increasing.

In a very large number of cases, the marker gene used is the lacZ gene which encodes E. coli β-gal. Another example of a marker gene which is also used is the gusA gene which encodes E. coli β-glu. Now, the substrates of the enzymes expressed by some of these genes, and in particular the lacZ and gusA genes, are saccharide derivatives. It is therefore very important to be able to provide saccharide substrates so as to be able to detect the activity of these enzymes.

Many substrates of saccharide nature already exist for detecting enzymatic activities such as, for example, β-gal and β-glu enzymatic activities. These enzymatic substrates may in particular be:

- substrates for nuclear imaging,
- chemiluminescent substrates such as the substrates sold under the trade names Lumi-Gal® 530 by the company Lumigen Inc. (USA) and Galacton-Star® by the company Applied-Biosystems (USA);
- substrates for dielectrophoretic detection,
- substrates for MRI,
- substrates forming precipitates,
- substrates for spectrophotometric assays, including the X-gal substrate (5-bromo-4-chloro-3-indolyl-beta-D-galactopyranoside) sold, for example, under the trade name BlueTech® by the company Mirador DNA Design Inc.; and
- fluorescent substrates.

Ideally, these substrates should have the following properties:
- rapid enzymatic reaction kinetics,
- a low Michaelis constant,
- a large difference between the properties of interest of the substrate and those of its product(s) (properties of interest: absorption for a chromogenic substrate, fluorescence for a fluorogenic substrate, etc.).

The advantage of fluorescent substrates, compared with the other substrates described above, is their detection sensitivity and the low cost of the instruments required to use them. They make it possible, in the same way as MRI, and under certain conditions, to carry out an in vivo enzymatic detection.

In general, fluorescent enzymatic substrates function according to the following principle: a substrate which is nonfluorescent in the detection wavelength range gives a fluorescent product in this wavelength range when it is placed in the presence of an enzyme of which it is desired to detect the activity and which is specific for the substrate used. It is therefore necessary to find fluorophores whose fluorescence is initially inhibited when they are grafted onto the substrate and which is capable of being released after reaction with the enzyme of which it is desired to detect the activity. The choice of commercially available fluorophores is therefore limited by this constraint of initial inhibition of the fluorescence when the fluorophore is attached to the enzymatic substrate.

In vivo, the recent development of optical methods opens up new horizons for functional imaging. It is now possible to follow, in real time and non-invasively, gene expression in animals, in particular in mice, after anesthesia. Optical imaging has a certain number of advantages compared with the other functional imaging techniques such as magnetic resonance imaging (MRI), positron emission tomography (PET) and single photon emission computed tomography (SPECT):

- it avoids the handling of radioactive molecules, thus doing away with the constraints and risks associated therewith (radioprotection, waste management, synchrotron source for PET markers);
- it does not require a large investment in terms of instruments;
- it exhibits good sensitivity compared with MRI, in terms of amount of label injected.

Optical imaging uses fluorescent enzymatic substrates.

When it is desired to detect the presence of an enzymatic activity in vivo, for example in a small laboratory animal such as the mouse, very few fluorescent molecules are available for this application. In fact, in order for the excitation light and the light emitted by the fluorophore to be able to pass through the tissues, it is advisable to use fluorophores that absorb and emit in the near infrared range, i.e. at a wavelength of between 640 and 900 nm. However, very few molecules that are fluorescent in this wavelength range are currently commercially available (limitation essentially to cyanins). The double constraint, namely the initial inhibition of the fluorescence when the fluorophore is attached to the substrate and the use of a fluorophore that absorbs and emits in the near infrared range, is without doubt responsible for the absence of a fluorescent enzymatic substrate of saccharide nature in this wavelength range.

In fact, the majority of fluorescent enzymatic substrates of saccharide nature that are currently available on the market are not constructed from fluorophore groups that absorb and emit in the near infrared range. It is, for example, possible to obtain:

- fluorescein-based substrates for detecting β-gal activity, among which mention may, for example, be made of FDG (fluorescein-di-β-D-galactopyranoside) (excitation 490 nm/emission 514 nm) or one of its derivatives;
- coumarin-based or umbelliferone-based substrates for detecting β-gal, β-glu or phosphatase activities, such as the substrates MUG (4-methyl-umbelliferone-β-D-galactopyranoside), DiFMUG (6,8-difluoro-4-methylumbelliferyl-β-D-galacto-pyranoside), MUP (4-methylumbelliferone phosphate), DiFMUP (6,8-difluoro-4-methyl-umbelliferyl phosphate) and derivatives (excitation 350-380 nm/emission 450-470 nm); or alternatively
- resorufin-based substrates and derivatives, in particular for detecting lipase (excitation 570 nm/emission 585).

Most of the fluorescent substrates currently sold function according to the principle represented in scheme A below:

SCHEME A

In this scheme, the fluorophore F is grafted in the anomeric position 1 (anomeric bond of β-configuration) onto a monosaccharide, β-glucopyranose, so as to form the enzymatic substrate. This substrate should be weakly fluorescent before the reaction with the enzyme. The fluorophore groups should therefore be chosen such that their fluorescence can be initially inhibited by the monosaccharide. The enzymatic reaction induces a cleavage of the anomeric bond and releases the fluorophore group. When the fluorophore group is moved away from the monosaccharide, its fluorescence is no longer inhibited and it can then emit a signal which is detected using a spectrofluorimeter. The emitted signal reflects the enzymatic activity and is, in a certain concentration range, proportional to the concentration of enzyme.

However, the substrates which function according to the principle reported in scheme A have a certain number of drawbacks:
  the choice of the fluorophore group is limited by the fact that its grafting onto the sugar must be able to inhibit its fluorescence; not all fluorophore groups have this property, in particular in the near infrared range when it is desired to be able to carry out an in vivo detection (see above);
  if the inhibition of the fluorescence by the sugar is not complete, the detection sensitivity of the system is mediocre. In order to remedy this problem, certain manufacturers propose substrates in which the fluorophore group is linked to 2 saccharide units via the anomeric position 1. An example of this type of substrate is FDG. By multiplying the number of saccharide units bound to the fluorophore group by 2, the initial inhibition of the fluorescence is effectively increased. Nevertheless, the release of the fluorophore group and therefore of the fluorescence then also requires two enzymatic cleavages instead of only one, and the detection sensitivity is therefore only slightly improved in such a system.

Oligosaccharide substrates also exist in which the two ends are functionalized with a fluorophore and a fluorescence inhibitor or with two fluorophore groups (Cottaz S. et al., Eur. J. Biochem., 2000, 267, 5593-5600). The substrates function according to the principle represented in scheme B below:

in which $R_1$ and $R_2$ represent, respectively, a fluorophore group and a fluorescence inhibitor, or alternatively two fluorophore groups.

However, such substrates are not entirely satisfactory since the initial inhibition of the fluorescence is not always complete and they use fluorophore groups which do not make it possible to carry out an in vivo detection.

The only enzymatic substrate that absorbs and emits in the near infrared range is the substrate DDAOG, which is a conjugate of β-galactosidase (G) and of 7-hydroxy-9H-(1,3-dichloro-9,9-dimethylacridin-2-one) (DDAO), used for detecting β-gal activity and sold by the company Molecular Probes (USA). This substrate absorbs at 645 nm and emits at 660 nm. Its method of functioning, as described by C.-H. Tung et al., Cancer Research, 2004, 64, 1579-1583, is represented in scheme C below:

-continued

DDAO
Excitation = 646 nm
Emission = 659 nm

However, although it absorbs and emits in the near infrared range, this particular substrate itself also has a certain number of drawbacks:

- its fluorescence, when the fluorophore group is bound to the saccharide unit, is not completely inhibited, which gives a background noise that is initially not insignificant and reduces the detection sensitivity. Thus, in the in vivo experiment reported in the article by C.-H. Tung et al., (mentioned above) it can be noted that the dose of DDAOG injected (0.5 mg) and the required exposure time (2 minutes) are very substantial compared to the conventional amounts and exposure times for applications of this type (in general, 10-50 μg of substrate injected for an exposure time of 20 to 100 ms);
- the absorption and emission spectra for DDAO are very narrow and very close to one another, which requires very good optical filtering for the detection of the signal relative to the initial background noise;
- the absorption and emission spectra for DDAO are not yet shifted into the red enough to be in an optimal optical window for forming in vivo imaging.

The inventors have therefore developed what forms the subject of the invention in order to remedy all these problems.

The inventors in fact gave themselves the aim of providing a fluorescent enzymatic substrate of saccharide nature which does not have the drawbacks of the substrates currently available and which can in particular be used for detecting enzymatic activities in vivo.

A subject of the present invention is therefore a fluorescent enzymatic substrate, characterized in that it corresponds to structure (I) below:

(I)

in which:

- S is a backbone of saccharide nature consisting of at least one saccharide unit and chosen from monosaccharides, oligosaccharides having from 2 to 9 saccharide units and polysaccharides having at least 10 saccharide units;
- $B_1$ and $B_2$, which may be identical or different, represent a spacer arm consisting of a linear or branched, saturated or unsaturated hydrocarbon-based chain optionally substituted, interrupted and/or ending with one or more heteroatoms chosen from N, O or S, and/or with one or more groups chosen from $C_1$-$C_4$ alkyl, $C_1$-$C_4$ alkoxy and aryl radicals or with one or more functions chosen from ether, ester, amide, carbonyl, carbamate, urea, thiourea and disulfide functions;
- m and n, independently of one another, are integers equal to 0 or 1;
- $F_1$ is a fluorophore group;
- $I_1$ is an inhibitor of the fluorescence of $F_1$;

it being understood that:

i) $F_1$ and $I_1$, either directly or by means of the spacer arms $B_1$ and/or $B_2$ when m and/or n=1, are both grafted onto the same saccharide unit of the backbone S;

ii) one of the groups $F_1$ and $I_1$ is grafted in the anomeric position 1 of said saccharide unit, the anomeric bond being without distinction in the α- or β-position, the other group $F_1$ or $I_1$ occupying any free position of the same saccharide unit; and iii) no phosphate chain, saccharide unit or nitrogenous base intercalates between the saccharide unit of the backbone S bearing the groups $F_1$ and $I_1$, and said groups $F_1$ and $I_1$.

The definition given above for $B_1$ and $B_2$ consequently excludes all spacer arms which would comprise (or would consist of) a phosphate chain, a saccharide unit or a nitrogenous base.

The enzymatic substrates in accordance with the invention and as described above exhibit a better initial inhibition of the fluorescence given the spatial proximity of the groups $F_1$ and $I_1$ since the latter are both grafted onto the same saccharide unit. The advantages provided by the enzymatic substrates of the invention are based on the fact that the fluorescence of the fluorophore group in the initial substrate (before action of an enzyme) is not inhibited by the backbone S, but mainly by the inhibitor $I_1$ present on the same saccharide unit as the fluorophore group $F_1$. This specific configuration makes it possible, compared with the substrates known in the prior art:

- to broaden the choice of fluorophore groups that can be used: the choice of such a group is no longer limited to groups whose fluorescence must initially be inhibited by the backbone S. The choice of available fluorophore groups is therefore much wider and may in particular extend to fluorophore groups which emit in the near infrared range;
- to increase the sensitivity of detection of the enzymatic activity: in fact, the fluorescence of the fluorophore group is inhibited by an object which has specifically this role and which is thus much more effective than when the inhibition must be carried out by the saccharide backbone;
- to increase the solubility of the substrate through the use of fluorophore groups that are much more soluble than the fluorophore groups currently commercially available and which are generally hydrophobic;
- to facilitate the conditions for using the substrate, through fluorophore groups that are insensitive to variations in pH or to the RedOx potential, and can therefore be used more readily in vivo. In fact, certain fluorophore groups conventionally used, such as fluorescein, have emission properties that are highly pH-dependent and therefore not readily compatible with an in vivo application where the intracellular conditions cannot be modified. By using fluorophore groups whose emission properties are relatively independent of the pH, of the RedOx potential or of the ion concentration, the signal acquisition conditions and the sensitivity in vivo are facilitated.

The saccharide units of the backbone S of the substrates of structure (I) in accordance with the invention can in particular be chosen from galactose, mannose, idose, talose, rhamnose, glucose, ribose and fucose, and amino or acid derivatives thereof, among which mention may be made of galactosamine, glucosamine, lactosamine, glucuronic acid, iduronic acid and sialic acid. They are preferably chosen from glucosamine, galactose and glucuronic acid.

When the backbone S is a monosaccharide, these saccharide units are used unitarily. On the other hand, they are linked to one another by glycosidic bonds when the backbone S is an oligosaccharide or a polysaccharide.

According to the invention, when the backbone S is an oligosaccharide, it is preferably chosen from oligosaccharides comprising from 4 to 9 saccharide units.

Optionally, i.e. when m and/or n=1, the groups $F_1$ and/or $I_1$ are linked to the saccharide unit by means of a spacer arm so as to promote the interaction between the substrate and its enzyme or the inhibition of the fluorescence.

Examples of preferred spacer arms $B_1$ are bifunctional arms, such that one of their two ends is a function that is reactive with respect to the conventional groups for activation of the anomeric position of the saccharide unit to which they must be attached (notable examples of groups for activation of the anomeric position: —Br, —SPh with Ph=phenyl; notable example of functions reactive with respect to these activation groups: —OH in particular), and their other end is a function (for example amine or thiol) that is reactive with respect to a grafting function borne by the fluorophore group $F_1$ or the inhibitor group $I_1$ (such as, for example, an N-hydroxysuccinimidyl, isothiocyanate, sulfotetrafluorophenyl ester (STP-ester), maleimide or haloacetamide function).

According to a specific embodiment of the invention, and when the groups $F_1$ and/or $I_1$ are directly linked to the end saccharide unit of the backbone S (m and/or n=0), then the group $F_1$ or $I_1$ which is in the anomeric position 1 of the saccharide unit is linked to the latter by means of a covalent bond involving at least one atom X chosen from oxygen, carbon, sulfur and nitrogen atoms.

When m=0 (respectively n=0), the group $F_1$ (respectively $I_1$) that does not occupy the anomeric position may also be linked to the saccharide unit of the backbone S by means of a covalent bond involving at least one atom X chosen from oxygen, carbon, sulfur and nitrogen atoms.

Thus, the groups $F_1$ and/or $I_1$ may, for example, be linked to the saccharide unit (possibly in the anomeric position) by means of an amide, ester, thioether or thioester bond, this list not being exhaustive. The free positions of the saccharide units of the backbone S, which comprise neither the fluorophore group $F_1$ nor the inhibitor group $I_1$, and which are not involved in a glycosidic bond, can without distinction be unsubstituted (—H or —OH) or else be substituted, for example, with an amine function or with a group resulting from the interaction of a hydroxyl function or of an amine function with a protective group such as those conventionally used in organic chemistry and described, for example, in the book by T. W. Greene et al., "Protective Groups in Organic Synthesis", Third Edition, Wiley Science (1999). Among such protective groups, mention may be in particular be made of the groups: acetyl; benzyl; aryl, and in particular aryl groups substituted with a radical chosen from alkyl chains containing from 1 to 40 carbon atoms; 2,2,2-trichloroethyloxycarbonyl (Troc); benzyloxycarbonyl (BzC); trichloroacetamidate (TCA); tert-butyloxy-carbonyl (BOC); fluoranylmethoxycarbonyl (Fmoc), and also silylated groups such as, for example, t-butyldimethylsilyl (tBDMS) and trimethylsilyl (TMS) groups.

Among the fluorophore groups $F_1$, mention may in particular be made of fluorescein (sodium fluoresceinate) and its derivatives such as fluorescein isothiocyanate (FITC); fluorescent dyes that absorb and emit in the near infrared (NIR) range, such as those sold under the names Fluorescent Red NIR 700 (excitation wavelength: 672 nm; emission wavelength: 735 nm) and Fluorescent Red NIR 730 (excitation wavelength: 680 nm; emission wavelength: 755 nm) by the company Sigma-Aldrich; Cy5 (n=2) and Cy7 (n=3) (Amersham); 7-hydroxy-9H-(1,3-dichloro-9,9-dimethyl-acridin-2-one) (DDAO), rhodamine and its derivatives such as tetramethyl rhodamine isothiocyanate (TRITC); fluorescent dyes comprising reactive amines, such as coumarins, among which mention may in particular be made of the succinimidyl ester of 6-((7-amino-4-methylcoumarin-3-acetyl)amino)hexanoic acid (AMCA); the fluorescent dyes sold under the trade names BODIPY®, such as BODIPY® FR-$Br_2$, BODIPY® R6G, BODIPY® TMR, BODIPY® TR and BODIPY® 530/550 (excitation wavelength/emission wavelength, in nm), 558/568, 564/570, 576/589, 581/591, 630/650 and 650/665 sold by the company Bio-Rad Inc. (USA), IRDye® 800 sold by the company Licor, and Alexa Fluoro 750 and Alexa Fluor® 633 sold by the company Molecular Probes; porphyrins; cyanins; oxazines and fluorescent nanoparticles, i.e. having emission properties such as "quantum dots", gold particles, polymer-based nanoparticles and oxide nanoparticles.

According to a particularly preferred embodiment of the invention, the group $F_1$ is chosen from fluorophore groups that absorb and emit in the near infrared range, i.e. that emit and absorb at a wavelength of between 640 and 900 nm. Among such groups, mention may in particular be made of the following fluorophore groups: the fluorescent dyes sold under the names Fluorescent Red NIR 700 (excitation wavelength (Ex.): 672 nm/emission wavelength (Em.): 735 nm) and Fluorescent Red NIR 730 (Ex.: 680 nm/Em.: 755 nm) by the company Sigma-Aldrich; Cy5 (n=2; Ex.: 680 nm/Em.: 755 nm) and Cy7 (n=3: Ex.: 747 nm/Em.: 775 nm) (Amersham); 7-hydroxy-9H-(1,3-dichloro-9,9-dimethylacridin-2-one) (DDAO) (Ex.: 646 nm/Em.: 659 nm), IRDye® 800 (Ex.: 778 Em.: 806 nm), Alexa Fluor® 750 (Ex.: 749 nm/Em.: 774 nm), Alexa Fluor® 633 (Ex.: 633 nm/Em.: 647 nm). According to a specific embodiment of the invention, the fluorophore group $F_1$ may also be functionalized with one or more groups chosen from lipophilic chains, phospholipids and peptides. Thus functionalized, the fluorophore groups $F_1$ have a greater affinity for the cells of animal tissues.

According to the invention, the group $I_1$ may be chosen from all compounds that accept the fluorescence of the group $F_1$, i.e. that allow a reduction or the complete disappearance of the fluorescence of the group $F_1$ when they are both attached to the same saccharide unit of the backbone S of the substrates of structure (I). This compound, of various natures, may in particular be a fluorescent or nonfluorescent chemical group or a nanoparticle.

When the group $I_1$ is itself a fluorescent group, then it is chosen from groups whose fluorescence inhibits that of the group $F_1$ (reference is then made to autoinhibition, the fluorescence of the group $I_1$ inhibiting that of the group $F_1$). In this case, the group $I_1$ is generally identical to the group $F_1$ and is chosen from cyanins, and the fluorophore groups Cy5, Cy7, IRDye® 800, Alexa Fluor® 750 and Alexa Fluor® 633. By way of group $I_1$. use may also be made of a fluorescent group, other than the group $F_1$, which absorbs the fluorescence of the group $F_1$ by fluorescence resonance energy transfer (FRET). In this case, the following $F_1/I_1$ pairs are preferably used: Cy5/Cy7; Cy5/Alexa Fluor® 750; Alexa Fluor® 633/Cy7; Alexa Fluor® 633/Alexa Fluor® 750; Cy7/IRDye® 800; Alexa Fluor® 750/IRDye® 800.

When the group $I_1$ is a nonfluorescent group, i.e. a fluorescence inhibitor per se (quencher), then it is preferably chosen from the compounds sold under the trade names Dabcyl® and derivatives, Black Hole Quencher® (BHQ), such as BHQ 1, BHQ 2, or BHQ 3 (Biosearch Technologies), Nanogold Particules® (Nanoprobes), Eclipse Dark Quencher® (Epoch Bioscience), Elle Quencher® (Oswell), Cy7Q (Amersham), FluoQuench®, such as FluoQuench® 660 and FluoQuench® 661 (FluoProbes), and the QSY® dyes such as QSY® 7, QSY® 9 and QSY® 21 (Molecular Probes).

According to the invention, the groups $F_1$ and $I_1$ are used as they are provided commercially, it being possible for these groups in particular to comprise, in addition to the chromophore part per se, a functional group for grafting, such as, for example, an N-succinimidyl function, a maleimide function, a carboxylic acid function, an amine function, etc., and optionally a spacer arm located between said grafting function and said chromophore part. The spacer arms $B_1$ and $B_2$ optionally present in the compounds of formula (I) in accordance with the invention are then other spacer arms that are incorporated between the grafting group of the groups $F_1$ and $I_1$ and the saccharide unit of the backbone S.

Thus, depending on the nature of the group $I_1$, and in the case where the groups $F_1$ and $I_1$ are both linked to the end saccharide unit of the backbone S by means of a spacer arm $B_1$ and $B_2$, respectively, the functioning principle of the enzymatic substrates of structure (I) in accordance with the invention can be represented by scheme D below:

2. Configuration 2: the quencher-type group $I_1$ is attached in the anomeric position 1 of a saccharide unit of a backbone S by means of a spacer arm $B_2$, the fluorophore group $F_1$ is attached in another position of the same saccharide unit of the backbone S by means of a spacer arm $B_1$, in the present case in position 2. The enzymatic cleavage releases the group $I_1$, from the backbone S. Moved away from the inhibitor, the fluorophore group $F_1$, which remains attached to the sugar backbone, emits. The advantage of such a configuration is that the group $F_1$ remains attached to the saccharide backbone which a priori remains located in the cell.

3. Configuration 3: the group $F_1$ is a fluorophore group attached in the anomeric position 1 of a saccharide unit of a backbone S by means of a spacer arm $B_1$; the group $I_1$ is a fluorescent group whose fluorescence inhibits the fluorescence of the group $F_1$, attached in another position of the same saccharide unit of the backbone S by means of a spacer arm $B_2$, in the present case at position 2. The enzymatic cleavage releases the group $F_1$ which finds itself moved away from $I_1$. $F_1$ is no longer inhibited by $I_1$. The two groups $F_1$ and $I_1$ emit. The advantage of such a structure is that the fluorescence observed is doubled. This configuration is particularly suitable for the detection of enzymatic activities of low intensity if $F_1$ is identical to $I_1$.

SCHEME D in which the groups $B_1$ and $B_2$, which may be identical to or different than one another, may have one of the meanings indicated above.

According to this scheme:
1. Configuration 1: the group $F_1$ is attached in the anomeric position 1 of a saccharide unit of a backbone S by means of a spacer arm $B_1$, the group $I_1$ is a quencher-type fluorescence inhibitor attached in another position of the same saccharide unit of the backbone S by means of a spacer arm $B_2$, in the present case in position 2. The enzymatic cleavage releases the fluorophore $F_1$ from the backbone S. Moved away from the inhibitor $I_1$, the fluorophore group $F_1$ emits.

4. Configuration 4: the saccharide unit of the backbone S comprising the groups $F_1$ and $I_1$ is linked, by a glycosidic bond, to at least one other saccharide unit, so as to form, for example, a tetrasaccharide.

Among the enzymatic substrates of structure (I) in accordance with the invention, preference is most particularly given to the compounds in which:
i) the backbone S is a galactosamine, and $F_1$ and $I_1$ are identical and are chosen from the groups Cy5, Alexa Fluor® 750, Cy7 and IRDye® 800, these groups being respectively attached in positions 1 and 2 of the galactosamine;

ii) the backbone S is a galactosamine, $F_1$ is a group Cy5, Alexa Fluor® 750, Alexa Fluoro 633 or IRDye® 800, and $I_1$ is a group QSY® 21, Cy7Q or BHQ3;

iii) the backbone S is a lactosamine, $F_1$ is a group Cy5, Cy7, Alexa Fluoro 750 or IRDye® 800, and $I_1$ is a group QSY® 21, Cy7Q or BHQ3;

iv) the backbone S is a trisaccharide comprising a glucosamine in the end position and in which the other two saccharide units, which may be identical or different, are chosen from galactose and fucose, $F_1$ is a group Cy5, Cy7, Alexa Fluor® 750 or IRDye® 800, and $I_1$ is a group QSY® 21, Cy7Q or BHQ3.

The enzymatic substrates of formula (I) in accordance with the invention, in which the groups $F_1$ and $I_1$ are different than one another, may for example be prepared according to a method (P1) comprising at least the following steps:

(i) in a first step, the backbone S, in which the anomeric position 1 is deprotected and the position on to which it is desired to graft the second functionality ($F_1$ or $I_1$) comprises a reactive function involving at least one atom X' (X'=N, O or S) protected with a protective group R such as those mentioned above (T. W. Greene et al., 1999, mentioned above), is subjected to a reaction for activation of the anomeric position (grafting of a group R' in position 1, R' representing a reactive function (R' represents, for example, —Br or —SPh with Ph=phenyl));

(ii) in a second step, the product obtained in step (i), in which the anomeric position is activated with R', is reacted:
either with a fluorophore group $F_1$ (respectively with an inhibitor $I_1$) comprising an end function (T, with T=—OH, for example) that is reactive with respect to the group R' in the anomeric position,
or, in a first step, with a bifunctional spacer arm comprising, at one of its ends, an end function (T) that is reactive with respect to the reactive function R' in the anomeric position, and at the other end a function (R", with R"=amine or thiol, for example) that is reactive with respect to a grafting function (G, with G=N-hydroxysuccinimidyl, isothiocyanate, sulfotetrafluorophenyl ester (STP-ester), maleimide or haloacetamide, for example) borne by the fluorophore group (respectively inhibitor group), which, in a second step, reacts with said reactive function R" of the spacer arm;

(iii) in a third step, a deprotection of the function —XR present on the position on to which it is desired to graft the second functionality is carried out by cleavage of the protective group R, so as to obtain a compound comprising a deprotected function —XH, (iv) in a fourth step, the product obtained above in step iii) is reacted:
either with an inhibitor group $I_1$ different than $F_1$ (respectively a fluorophore group $F_1$ different than $I_1$) comprising an end function (T) that is reactive with the function —XH,
or, in a first step, with a bifunctional spacer arm comprising at one of its ends an end function (T) that is reactive with respect to the function —XH, and at the other end a function (R") that is reactive with respect to a grafting function (G) borne by the inhibitor group (respectively fluorophore group), which, in a second step, reacts with said reactive function (R") of the spacer arm, so as to obtain the corresponding compound of structure (I).

This method P1 is represented in scheme E below:

SCHEME E

The method P1 represented in scheme E above comprises a minimum number of steps. It should, however, be clearly understood that, depending on the nature of the enzymatic substrate of formula (I) that it is desired to obtain, additional protection/deprotection reactions may be necessary. These reactions are carried out conventionally, according to the methods known to those skilled in the art.

According to this method, it should also be understood that the spacer arms $B_1$ and $B_2$, when both are present, may be identical to or different than one another.

Moreover, although this method of synthesis P1 is particularly suitable for the synthesis of enzymatic substrates of formula (I) in which the groups $F_1$ and $I_1$ are different than one another, it is, however, also entirely useable for the preparation of enzymatic substrates of formula (I) in which the groups $F_1$ and $I_1$ are identical, in particular when these groups are attached to the saccharide unit by means of spacer arms $B_1$ and $B_2$ with $B_1$ different than $B_2$.

The enzymatic substrates of formula (I) in accordance with the invention in which the groups $F_1$ and $I_1$ are identical can also be prepared, for example, according to a method P2 comprising at least the following steps:

(i) in a first step, the backbone S, in which the anomeric position 1 is deprotected and the position on to which it is desired to graft the second functionality ($F_1$ or $I_1$) comprises a function involving at least one atom X' (X'=N, O or S) protected with a protective group R such as those mentioned above, is subjected to a reaction for activation of the anomeric position (grafting of a group R' in position 1, R' representing a reactive function (R' represents, for example, —Br or —SPh with Ph=phenyl));

ii) in a second step, a deprotection of the function —XR present on the position on to which it is desired to graft the second functionality is carried out by cleavage of the protective group R, so as to obtain a compound comprising a deprotected function —XH;

(iii) in a third step, the product obtained in step (ii), in which the anomeric position is activated with R' and which comprises a deprotected function —XH, is reacted:

either with a fluorophore group $F_1$ ($F_1=I_1$) comprising an end function (T, with T=—OH, for example) that is reactive with respect to the group R' in the anomeric position and to the deprotected function —XH, so as to obtain a compound bifunctionalized with a group $F_1$ (with $F_1=I_1$), or, in a first step, with a bifunctional spacer arm comprising at one of its ends an end function (T) that is reactive with respect to the reactive function R' in the anomeric position and to the deprotected function —XH, and at the other end a function (R'', with R''=amine or thiol, for example) that is reactive with respect to a grafting function G as defined above, borne by the fluorophore group ($F_1=I_1$) which, in a second step, reacts with said reactive function (R'') of the spacer arm;

so as to obtain an enzymatic substrate of formula (I) in which $F_1=I_1$ and in which, when they are present, $B_1=B_2$ This method P2 is therefore particularly suitable when the enzymatic substrates comprise fluorophore $F_1$ and inhibitor $I_1$ groups which are identical to one another since they are grafted on to the saccharide unit simultaneously, optionally by means of a spacer arm, also identical from one group to the other. This method P2 is represented in scheme F below:

SCHEME F iii) - either B (with $B_1 = B_2$) if m = n = 1
- or $F_1$ ( = $I_1$) if m = n = 0 m ( = n) = 0 or 1
B = $B_1$ = $B_2$
m ( = n) = 0 or 1

According to a variant of the invention, this method P2 may also be used for the preparation of enzymatic substrates of formula (I) in which the groups $F_1$ and $I_1$ are not necessarily identical to one another. In this case, step iii) is carried out in the presence of a mixture of $F_1$ and $I_1$ (with $F_1$ different than $I_1$) and results in the production of a library of 4 enzymatic substrates of formula (I) doubly labeled and different than one another:

Enzymatic substrate (Ia): backbone S in which the end saccharide unit is doubly labeled with a group $F_1$ (one in the anomeric position and the other on another position of the same saccharide unit);

Enzymatic substrate (Ib): backbone S in which the end saccharide unit is doubly labeled with a group $I_1$ (one in the anomeric position and the other on another position of the same saccharide unit);

Enzymatic substrate (Ic): backbone S in which the end saccharide unit is labeled with a group $F_1$ in the anomeric position and with a group $I_1$ on another position of the same saccharide unit;

Enzymatic substrate (Id): backbone S in which the end saccharide unit is labeled with a group $I_1$ in the anomeric position and with a group $F_1$ on another position of the same saccharide unit.

These enzymatic substrates (Ia) to (Id) can be separated from one another by conventional separative techniques well known to those skilled in the art, such as high performance liquid chromatography (HPLC), silica chromatography, or charge separation. After separation, these substrates can be purified and studied independently.

In the specific case where the groups $F_1$ and $I_1$ also carry opposite charges (for example, $F_1$=negatively charged Cy5 and $I_1$=positively charged QSY® 21), it is then possible to benefit from the following advantages:

The separation of the four enzymatic substrates is facilitated. A negatively charged enzymatic substrate of type (Ia) ($F_1=I_1$=Cy5), a positively charged enzymatic substrate of type (Ib) ($F_1=I_1$=QSY® 21) and 2 enzymatic substrates of type (Ic) and (Id) which are neutral (Cy5 in the anomeric position and QSY® 21 on another position, and QSY® 21 in the anomeric position and Cy5 on another position) are in fact obtained. Thus, the charged enzymatic substrates can be separated from the neutral enzymatic substrates by charge separation by gel chromatography. The neutral enzymatic substrates can be separated from one another by HPLC or by silica column chromatography, although it is also possible to use the mixture of the two enzymatic substrates as it is;

the two enzymatic substrates may have advantages for the detection of enzymatic activities in vivo. In fact, a neutral molecule will penetrate into the intracellular medium more successfully. On the other hand, the enzymatic degradation of these substrates will, in this case, produce two charge molecules which will be retained more successfully in the intracellular medium than a neutral molecule.

According to a variant of the method P2, step iii) can also be carried out using a mixture containing several groups $F_1$ ($pF_1$ with p=number of different groups $F_1$) and several groups $I_1$ ($qI_1$ with q=number of different groups $I_1$), in a combinatorial chemistry approach. Statistically, $(p+q^2)$ different enzymatic substrates of formula (I) are then obtained, which can subsequently be separated (for example, by HPLC purification, silica chromatography, charge separation). After separation, these various enzymatic substrates can be purified and studied independently from one another. A library of $(p+q)^2$ enzymatic substrates of formula (I), the in vivo imaging potential of which can subsequently be evaluated via a screening, is thus obtained.

At each step of these methods P1 and P2, the intermediate compounds, and the final compound(s) of structure (I) at the end of synthesis, are preferably washed, isolated and purified according to methods conventionally used for this purpose, such as, for example, column purification.

By way of example, and when the backbone S of the compounds of formula (I) is a monosaccharide such as galactosamine, n=0, m=1 with $B_1$=—$CH_2$—$CH_2$—NH and $F_1$ and $I_1$ are both fluorescent groups, which may be identical to or different than one another, the compounds in accordance with the invention can also be synthesized using the general synthesis scheme G below:

In this scheme, the abbreviations used have the following meaning:
- TrocCl: 2,2,2-trichloroethyloxycarbonyl chloride,
- NaHCO$_3$: sodium hydrogen carbonate,
- Ac$_2$O: acetic anhydride,
- pyr: pyridine,
- F: fluorescent group (F, F$_1$ or F$_2$),
- N-Fmoc ethanolamine: N-α-fluoranylmethoxycarbonyl ethanolamine,
- BF$_3$.Et$_2$O: boron trifluoride etherate,
- CH$_2$Cl$_2$: dichloromethane (DCM),
- Zn: zinc,
- AcOH: acetic acid,
- DIEA: diisopropylethylamine,
- DMF: dimethylformamide,
- NaOH: sodium hydroxide,
- MeOH: methanol,
- Et$_3$N: triethylamine.

As has been amply described and explained above, the enzymatic substrates of structure (I) in accordance with the invention can be used for the detection of an enzymatic activity in vitro and in vivo.

A second subject of the present invention is therefore the use of at least one enzymatic substrate of structure (I) as defined above, as a fluorescent reagent for detecting an enzymatic activity in vitro.

According to a particularly preferred embodiment, the fluorophore group F$_1$ of the enzymatic substrates of structure (I) is chosen from groups that absorb and emit in the near infrared range, in particular between 640 and 900 nm, so as to allow use in vivo. In this case, a subject of the present invention is also the use of at least one enzymatic substrate of structure (I) in which the fluorophore group F, is chosen from groups that absorb and emit in the near infrared range, for preparing a diagnostic reagent intended for functional imaging in vivo, and in particular for imaging, by fluorescence, the expression of the E. coli lacZ and gusA reporter genes.

Finally, a subject of the invention is a diagnostic reagent, characterized in that it comprises at least one solution consisting of water or of a mixture of water and at least one organic solvent, said solution containing at least one enzymatic substrate of structure (I) as defined above.

According to a specific and preferred embodiment of the invention, the reagent is an in vivo diagnostic reagent and the enzymatic substrate of structure (I) comprises at least one fluorophore group F, chosen from fluorophore groups that absorb and emit in the near infrared range.

By way of organic solvents that can be used, mention may be made of the solvents conventionally used for preparing diagnostic reagents, among which are, for example, lower alcohols such as ethanol and dimethyl sulfoxide (DMSO). When they are used, these solvents can represent up to 50% (by volume) of the solution containing the enzymatic substrate of structure (I).

According to a specific embodiment of the invention, the solution may also contain a physiologically acceptable buffer such as a phosphate buffer, for instance PBS ("Phosphate Buffered Saline") at pH 7.2.

Within the diagnostic reagent in accordance with the invention, the concentration of the enzymatic substrate(s) of structure (I) is preferably between approximately 1 μM and 1 mM, more preferably between approximately 10 μM and 200 μM. According to a particularly preferred embodiment of the invention, this concentration is approximately 100 μM.

In addition to the above arrangements, the invention also comprises other arrangements which will emerge from the description which follows, which refers to examples of preparation and of use of fluorescent saccharide substrates of formula (I) in accordance with the invention, and also to the attached FIGS. 1 to 6 in which.

EXAMPLE 1

Synthesis and Use of the Compound of Formula (5a): Gal(N-Cy5)-Cy5

(5a)

(S=galactosamine, m=n=0, F$_1$–I$_1$=Cy5)

I) Synthesis

1) First step: Synthesis of 1,3,4,6-tetra-O-acetyl-2-deoxy-2-(2,2,2-trichloroethoxycarbonylamino)-β-D-galactopyranose (1)

(1)

0.65 g (3 eq.) of sodium hydrogen carbonate and 0.43 ml (1.2 eq.) of trichloroethoxycarbonyl chloride were added, dropwise, to a solution of 0.5 g of galactosamine (2.32 mmol) in 6 ml of distilled water. The reaction medium was stirred for 1 hour and then the solvent was evaporated off under vacuum. The residue obtained was then dissolved in 15 ml of pyridine and 2 ml (8 eq.) of acetic anhydride were then added. The reaction medium was stirred for 15 hours and then the solvent was evaporated off under reduced pressure. The crude product was chromatographed on silica gel (eluent: cyclohexane/ ethyl acetate (EtOAc): 3/2, v/v) to give 11.1 g (2.11 mmol) of the expected compound (1) with a yield of 91%.

The structural analysis of the product obtained was in accordance with that of the expected product:

$^1$H NMR (CDCl$_3$): δ=6.30 (d, 1H, NHTroc, $J_{NHTroc,2}$=3.5 Hz); 5.46 (m, 1H, H-4); 5.23 (m, 2H, H-] and H-3); 4.76 (s, 2H, COO—CH$_2$—CCl$_3$); 4.48 (m, 1H, H-2); 4.42 (dd, 1H, H-6A, $J_{6a-6b}$=11.2 Hz, $J_{6a,5}$=4.0 Hz); 4.28 (m, 1H, H-5); 4.23 (dd, 1H, H-6b, J6b.5, =4.5 Hz); 2.22 (s, 3H, CH$_3$CO); 2.15 (S, 3H, CH$_3$CO); 2.07 (s, 3H, CH$_3$—CO); 2.11 (s, 3H, CH$_3$—CO).

$^{13}$C NMR (CDCl$_3$): δ=170.7; 170.6; 169.3; 149.6; 95.7; 91.5; 68.9; 68.2; 67.0; 61.6; 21.0

ESI: m/z=523 [M+H]$^+$

2) Second step: Synthesis of 2-hydroxy-N-9-fluorenyl-methoxycarbonyl-1-aminoethyl-3,4,6-tri-O-acetyl-2-deoxy-2-(2,2,2-trichloroethoxycarbonylamino)-β-D-galactopyranose (2)

(2)

0.6 g (1.15 eq.) of 1,3,4,6-tetra-O-acetyl-2-deoxy-2-(2,2, 2-trichloroethoxycarbonylamino)-β-D-galacto-pyranose (1) obtained above in step 1) was dissolved in 15 ml of anhydrous dichloromethane and then 400 mg (1.2 eq.) of N-Fmoc ethanolamine and 0.45 ml (3 eq.) of boron trifluoroetherate (BF$_3$.Et$_2$O) were added. The reaction mixture was stirred for 5 hours, diluted in dichloromethane (DCM), and then washed with a solution of HCl (1M). The organic phases were combined, dried, and concentrated under reduced pressure. The crude product obtained was then purified by chromatography on silica gel (eluent: cyclohexane/EtOAc 2/1: v/v). The compound (2) (0.53 g; 0.71 mmol) was then isolated with a yield of 62%.

The structural analysis of the product obtained was in accordance with that of the expected product:

$^1$H NMR (CDCl$_3$): δ=7.78 (m, 2H, Ha); 7.61 (m, 2H, Hd); 7.35 (m, 4H, Hc and Hd); 5.44 (m, 1H, NHFmoc); 5.30 (d, 1H, H-4, $J_{4,3}$=3.5 Hz); 5.23 (d, 1H, H-1, $J_{1,2}$=8.9 Hz); 5.12 (dd, 1H, H-3, $J_{3,2}$=11.1 Hz); 4.70 (m, 3H, H-5 and COOCH$_2$CCl$_3$); 4.39 (m, 2H, NHT$_{roc}$ and H-6a); 4.21 (m, 1H, H-6b); 4.03 (d, 2H, Hf, $J_{f,e}$=6.8 Hz); 3.90 (dd, 1H, H-2, $J_{2,3}$=11.1 Hz); 3.76 (m, 2H, O—CH$_2$—CH$_2$—N); 3.53 (t, 1H, He); 3.36 (m, 2H, O—CH$_2$—CH$_2$—N); 2.15 (s, 3H, CH$_3$CO); 2.00 (s, 3H, CH$_3$CO); 1.90 (s, 3H, CH$_3$CO).

$^{13}$C NMR (CDCl$_3$): δ=170.7; 171.0; 157.1; 155.0; 144.2; 141.7; 128.2; 127.6; 125.3; 120.4; 102.0; 96.0; 74.7; 71.0; 70.3; 67.0; 66.7; 66.3; 62.2; 53.0; 47.7; 41.4; 27.3; 21.1.

ESI: m/z=745 [M+H]$^+$

3) Third step: Synthesis of 2-hydroxy-N-9-fluorenyl-methoxycarbonyl-1-aminoethyl-3,4,6-tri-O-acetyl-2-deoxy-2-amino-β-D-galactopyranose (3)

(3)

0.15 g of activated zinc was added to 0.2 g (0.34 mmol) of 2-hydroxy-N-9-fluorenylmethoxycarbonyl-1-aminoethyl-3, 4,6-tri-O-acetyl-2-deoxy-2-(2,2,2-trichloroethoxy-carbonylamino)-β-D-galactopyranose (2) obtained above in step 2), solubilized in 4 ml of acetic acid. The reaction mixture was stirred for 6 hours and the zinc was then removed by filtration over celite. The filtrate was concentrated under reduced pressure and the product was crystallized from ethyl ether. 0.12 g (0.27 mmol) of compound (3) was then obtained with a yield of 79%.

The structural analysis of the product was in accordance with that of the expected product:

$^1$H NMR (CDCl$_3$): δ=7.74 (m, 2H, Ha); 7.58 (m, 2H, Hd); 7.34 (m, 4H, Hc and Hd); 5.85 (m, 1H, NHFmoc); 5.36 (d, 1H, H-4, $J_{4,3}$=3.3 Hz); 5.25 (d, 1H, H-1, $J_{1,2}$=9.2 Hz); 4.86 (m, 2H, H-3 and H-5); 4.20 (m, 2H, H-6); 4.03 (d, 2H, Hf, $J_{f,e}$=6.8 Hz); 4.00 (m, 2H, O—CH$_2$—CH$_2$—N); 3.90 (dd, 1H, H-2); 3.53 (m, 1H, He); 3.40 (m, 2H, O—CH$_2$—CH$_2$—N); 2.07 (s, 3H, CH$_3$CO); 2.04 (s, 3H, CH$_3$CO); 1.87 (s, 3H, CH$_3$CO).

$^{13}$C NMR (CDCl$_3$): δ=170.6; 170.4; 170.9; 144.1; 141.5; 127.9; 127.4; 125.2; 120.2; 100.6; 71.0; 69.8; 68.2; 66.5; 61.8; 52.9; 47.3; 41.3; 21.3; 20.8; 20.7.

ESI: m/z=571 [M+H]$^+$

4) Fourth step: Synthesis of 1-aminoethyl-2-amino-2-deoxy-β-D-galactopyranose (4)

(4)

0.1 g (0.17 mmol) of 2-hydroxy-N-9-fluorenylmethoxy-carbonyl-1-aminoethyl-3,4,6-tri-O-acetyl-2-deoxy-2-amino-β-D-galactopyranose (3) as obtained above in step 3) was dissolved in 5 ml of methanol and then 13.6 ml (8 eq.) of a 1N sodium hydroxide solution were added. The reaction mixture was stirred for 1 hour and then neutralized by adding a cation exchange resin sold under the name Dowex 50WX8 by the company Sigma-Aldrich. The resin was then removed by filtration through sintered glass and the filtrate was concentrated under reduced pressure. 0.32 g (0.14 mmol) of compound (4) was then isolated by crystallization from DCM with a yield of 84%.

The structural analysis of the product obtained was in accordance with that of the expected product:

$^1$H NMR (D$_2$O): δ=4.19 (d, 1H, H-1, J$_{1,2}$=8.1 Hz); 3.85 (m, 1H, H-4); 3.68 (dd, 1H, H-3, J$_{3,4}$=4.7 Hz; J$_{3,2}$=11.9 Hz); 3.58 (m, 3H, H-5 and O—CH$_2$—CH$_2$—N); 3.49 (m, 4H, H-6 and O—CH$_2$—CH$_2$—N); 3.68 (dd, 1H, H-2).

$^{13}$C NMR (D$_2$O): δ=103.2; 75.5; 73.0; 69.2; 68.1; 61.2; 53.2; 40.0.

ESI: m/z=223 [M+H]+

5) Fifth Step: Obtaining the Compound of Formula (5a), Gal(N-Cy5)-Cy5

0.13 mg (5.85×10$^{-4}$ mmol) of 1-aminoethyl-2-amino-2-deoxy-β-D-galactopyranose (4) as obtained above in step 4) and 50 µl of triethylamine were added to a solution of Cy5NHS (1 mg; 1.14×10$^{-3}$ mmol) dissolved in 200 µl of dimethyl sulfoxide (DMSO). The reaction medium was stirred for 15 hours and then concentrated under reduced pressure. The compound (5a) was then obtained after purification by high performance liquid chromatography (HPLC).

The structural analysis of the product obtained was in accordance with that of the expected product:

ESI: m/z=1581 [M+H]$^+$

Figure 1:
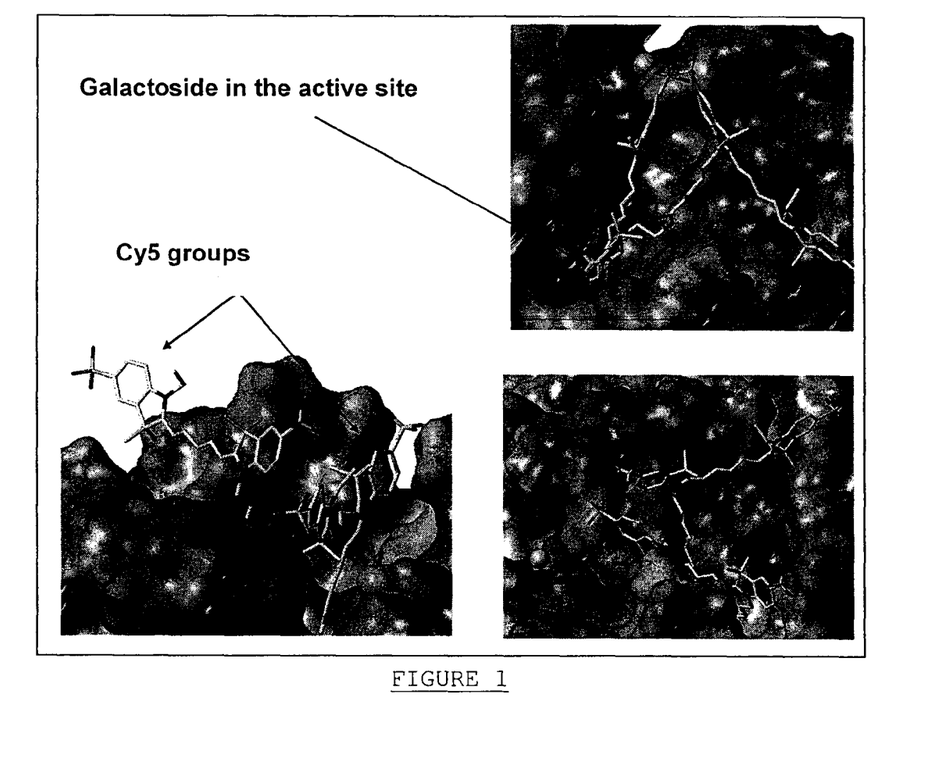
FIG. 1 represents the molecular modeling of a complex between β-galactosidase and a galactoside grafted with two Cy5 groups using the modeling software sold under the trade name Sybyl® 7.0 by the company Tripos Inc.

II) Use of the Compound of Formula (5a) for Detecting the Enzymatic Activity of β-Galactosidase II-1) Detection of the Enzymatic Activity by Molecular Modeling Molecular modeling of the interactions between β-galactosidase (β-gal) and the compound of formula (5a), Gal(N-Cy5)-(Cy5), was carried out in order to determine the potentialities of this product as a substrate for this enzyme.

The data used for the modeling of the enzyme are derived from the study by D. Juers et al. (Code PDB 1JYV, Juers D H, Heightman T D, Vasella A, et al. "A structural view of the action of Escherichia coli (lacZ) β-galactosidase.", Biochemistry, 2001, 40, 14781-14794) giving the crystallographic coordinates for 1-gal undergoing interaction with a calorimetric substrate: ortho-nitrophenylgalactopyranoside (ONPG). The galactose molecule functionalized with two Cy5 groups was constructed in the modeling software sold under the trade name Sybyl® 7.0 by the company Tripos Inc. using the available molecule editor, and adding the chemical groups to a galactose originating from the Cermav three-dimensional databank (http://www.cermav.cnrs.fr/glyco3d). The two Cy5 groups were constructed in extended conformations. This molecule was then placed in the active site of the enzyme in place of the original substrate, ONPG.

The results obtained are given in the attached FIG. 1.

They show that the two arms of the Cy5 groups in the extended confirmation generate only very little steric conflict with the protein. The geometry of the complex could therefore be directly optimized so as to obtain a low-energy configuration (the charges of the protein were assigned according to the Kollman charge library, those assigned to the substrate are derived from the Gasteiger-Huckel library). Only the side chains of the amino acids close to the binding site and the Cy5 molecule were optimized. The configuration represented in FIG. 1 has an energy that is sufficiently low for one to be able to consider that the formation of this complex is possible. In fact, even if the active site of the enzyme is relatively deep, the length of the alkyl chains (from 6 to 9 carbon atoms) linking the galactose to the two Cy5 groups is sufficient to allow these cyanin groups to be located at the surface of the protein.

Thus, it is possible to consider that the compound (5a) in accordance with the present invention may indeed be a substrate for the β-gal enzyme.

II-2) Use of the Compound (5a) for Detecting the Enzymatic Activity of β-Galactosidase: In Vitro Assay The enzymatic activity of β-galactosidase with respect to the compound of formula (5a) in accordance with the invention: Gal(N-Cy5)-(Cy5), was also tested in vitro.

The functioning principle of the novel enzymatic substrates of formula (I) in accordance with the invention is represented in scheme H below:

SCHEME H

The spatial proximity between two Cy5 produces an initial inhibition of their fluorescence. The fluorescence is recovered after enzymatic cleavage of the substrate.

A solution of the compound of formula (5a) at 1 µM, in 1.5 ml of phosphate buffer (PBS) at pH 7.4 was, moreover, prepared, and 15 international units (IU) of β-galactosidase were added thereto. The fluorescence was then measured at a wavelength of 665 nm, as a function of the incubation time at 20° C., using a fluorimeter sold under the trade name LS50B by the company Perkin Elmer.

Figure 2:
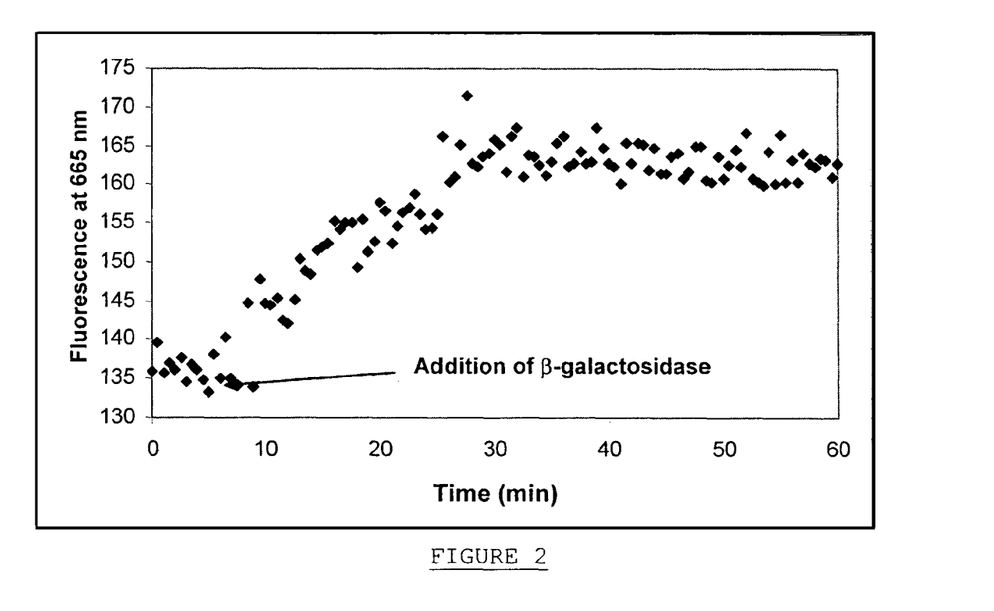
FIG. 2 represents the fluorescence (arbitrary units) measured at 665 nm as a function of time in minutes, when β-galactosidase (15 IU) is added to a solution of the compound of formula (5a) at 1 μM, in 1.5 ml of phosphate buffer (PBS) at pH 7.4 and at a temperature of 20° C.

The results obtained are given in the attached FIG. 2, in which the fluorescence measured in arbitrary units is expressed as a function of the time in minutes.

In this figure, an increase in fluorescence (+25%) is observed when β-galactosidase is added to the solution of compound of formula (5a), with a pseudo-1st order kinetic constant of 17 minutes, which confirms the predictions obtained by molecular modeling.

EXAMPLE 2

Synthesis and Properties of the Compound of Formula (8a): Gal(N-QSY® 21)-Alexa Fluoro 633

(8a)

(S=galactosamine, m=n=0, F, =Alexa Fluor® 633, I$_1$=QSY® 21)

I) Synthesis

This synthesis is carried out using the intermediate compound of formula (3), the preparation of which was described above in step 3) of example 1.

1) First Step: Synthesis of the Intermediate Compound of Formula (6a): Peracetylated Gal(N-QSY® 21)-NHFmoc (6a)

1 mg of QSY® 21 NHS (1 eq.) dissolved beforehand in 100 µl of anhydrous DMF was added to a solution of 0.7 mg ($1.22 \times 10^{-3}$ mmol) of 2-hydroxy-N-9-fluorenyl-methoxycarbonyl-]-aminoethyl-3,4,6-tri-O-acetyl-2-deoxy-2-amino-β-D-galactopyranose (3) as obtained above in step 3) of example 1, solubilized in 70 µl of anhydrous DMF. 50 µl of diisopropylethylamine (DIEA) were then added and the reaction mixture was then stirred for 15 hours. The solvent was then evaporated off under reduced pressure and the compound (6a) was obtained after purification by HPLC.

The structural analysis the product obtained was in accordance with that of the expected product:

ESI: m/z=1235 $[M+H]^+$

2) Second Step: Synthesis of the Intermediate Compound of Formula (7a): Gal(N-QSY® 21)-$NH_2$ (7a)

The peracetylated Gal(N-QSY® 21)-NHFmoc of formula (6a) was solubilized in 600 µl of a methanol/water/triethylamine mixture (MeOH/$H_2$O/TEA: 4/1/1). The reaction medium was stirred for 15 hours and then concentrated under reduced pressure. The compound (7a) was then obtained after purification by HPLC.

The structural analysis of the product obtained was in accordance with that of the expected product:

ESI: m/z=887 $[M+H]^+$

3) Third Step: Obtaining the Compound of Formula (8a): Gal(N-QSY® 21)-Alexa Fluoro 633

1 mg (1 eq.) of Alexa Fluor® 633NHS, dissolved beforehand in 100 µl of anhydrous DMF, and 50 µl of DIEA were added to a solution of 1.1 mg ($1.14 \times 10^{-3}$ mmol) of Gal(N-QSY® 21)-$NH_2$ of formula (7a) obtained above in the preceding step, solubilized in 100 µl of anhydrous DMF. The reaction mixture was stirred for 15 hours and then concentrated under reduced pressure. The compound of formula (8a) was then obtained after purification by HPLC.

The structural analysis of the product obtained was in accordance with that of the expected product:

ESI: m/z=930 $[M+3H]^{+}/2$

II) Photophysical Properties of the Compound of Formula (8a)

The IR absorption spectrum of the compound of formula (8a) was determined in solution at 3.5 µM in PBS (highest solid curve), compared with those of Alexa Fluor® 633 alone in solution at 3.5 µM in PBS (intermediate solid curve), of QSY® 21 alone in solution at 3.5 µM in methanol (lowest solid curve) and of the mixture QSY® 21 at 3.5 µM/Alexa Fluor® 633 at 3.5 µM in solution in PBS (dashed curve), using an apparatus sold under the name Cary 300 by the company Varian.

Figure 3:
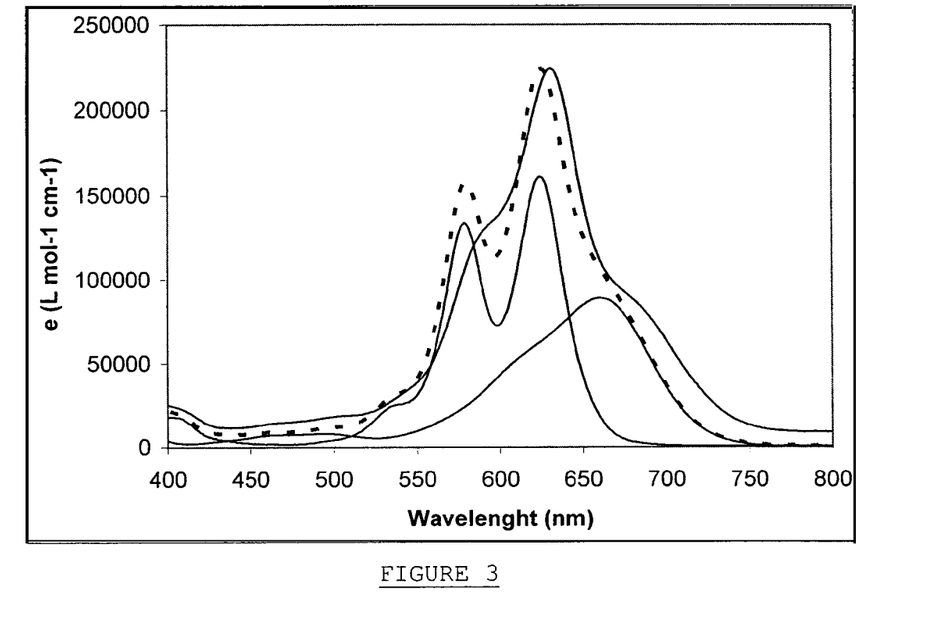
FIG. 3 represents the absorption spectra of the compound of formula (8a) in solution at 3.5 μM in 10 mM phosphate buffer, pH 7.2 (PBS) (highest solid curve), compared with those of Alexa Fluor® 633 alone in solution at 3.5 μM in PBS (intermediate solid curve), of QSY® 21 alone in solution at 3.5 μM in methanol (lowest solid curve) and of the mixture QSY® 21 at 3.5 μM/Alexa Fluor® 633 at 3.5 μM in solution in PBS (dashed curve). In this figure, the absorption e (in L mol$^{-1}$ cm$^{-1}$) is expressed as a function of the wavelength (nm)

The corresponding spectra are reported in the attached FIG. 3, in which the absorption (L $mol^{-1}$ $cm^{-1}$) is expressed as a function of the wavelength (nm).

These spectra confirm that there has indeed been grafting both of the Alexa Fluor® 633 fluorophore and of the QSY® 21 fluorescence inhibitor on to the galactosamine.

Figure 4:
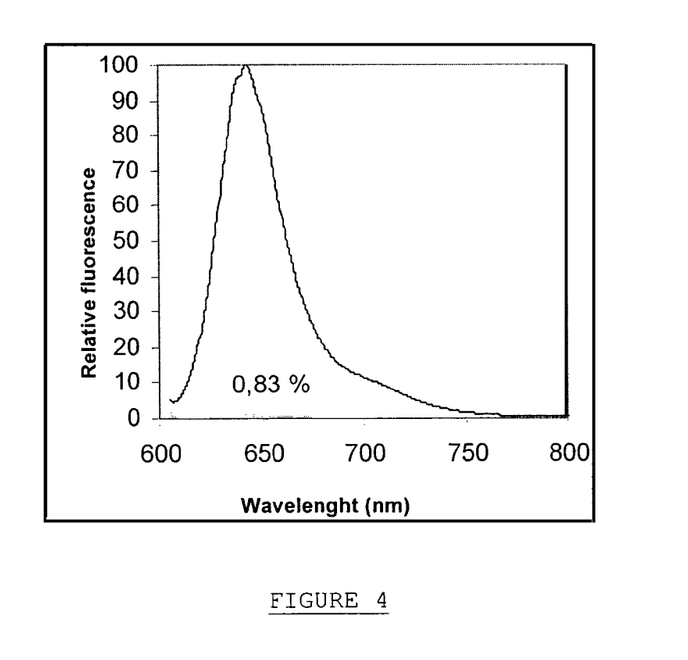
FIG. 4 represents the emission spectra (after excitation at 600 nm) of the compound of formula (8a) (lowest curve, almost nonexistent) compared with Alexa Fluor® 633 (highest curve). In this figure, the fluorescence (arbitrary units) is expressed as a function of the wavelength (nm)

The emission spectra of the compound of formula (8a) and of the Alexa Fluor® 633, after excitation at a wavelength of 600 nm, were also measured and are given in the attached FIG. 4, in which the relative fluorescence (arbitrary units) is expressed as a function of the wavelength (in nm). In this figure, the top curve represents the fluorescence observed for Alexa Fluoro 633, and the bottom curve, which is virtually nonexistent, represents that of the compound of formula (8a).

These results show that the proximity of the fluorescence inhibitor indeed produces inhibition of the fluorescence of the fluorophore (99.2% inhibition).

EXAMPLE 3

Synthesis and Properties of the Compound of Formula (8a): Gal(N-Cy5)-QSY® 21

(8b)

S=galactosamine; m=n=0; $F_1$=QSY® 21 and $I_1$=Cy5

This synthesis is carried out using the intermediate compound of formula (3), the synthesis of which is described above in step 3) of example 1.

1) First Step: Synthesis of the Intermediate Compound of Formula (6b): Peracetylated Gal(N-Cy5)-NHFmoc (6b)

1 mg of Cy5NHS (1 eq.), dissolved beforehand in 50 µl of anhydrous DMF, was added to a solution of 0.7 mg ($1.26 \times 10^{-3}$ mmol) of 2-hydroxy-N-9-fluorenylmethoxy-carbonyl-1-aminoethyl-3,4,6-tri-O-acetyl-2-deoxy-2-amino-β-D-galactopyranose of formula (3) as obtained above in step 3) of example 1, in 70 µl of anhydrous DMF. 50 µl of DIEA were then added and the reaction mixture was then stirred for 15 hours. The solvent was then evaporated off under reduced pressure and the compound of formula (6b) was obtained after purification by HPLC.

The structural analysis of the product obtained was in accordance with that of the expected product:

ESI: m/z=1248 $[M+H]^+$

2) Second Step: Synthesis of the Intermediate (7b): Gal(N-Cy5)-$NH_2$ (7b)

The peracetylated Gal(N-Cy5)-NHFmoc of formula (6b) obtained above in the first step was solubilized in 300 µl of a mixture of MeOH/$H_2$O/TEA:4/2/1 (v/v/v). The reaction mixture was stirred for 15 hours and then concentrated under reduced pressure. The compound of formula (7b) was then obtained after purification by HPLC.

The structural analysis of the product obtained was in accordance with that of the expected product:

ESI: m/z=901 [M+H]$^+$

3) Third Step: Obtaining the Compound of Formula (8b): Gal(N-Cy5)-QSY 1 mg (1 eq.) of Cy5NHS, dissolved in 100 μl of anhydrous DMF, and 50 μl of DIEA were added to a solution of 1 mg (1.11×10$^{-3}$ mmol) of Gal (N-Cy5)-NH$_2$ of formula (7b) as obtained above in preceding step 2), in 100 μl of anhydrous DMF. The reaction mixture was stirred for 15 hours and then concentrated under reduced pressure. The compound of formula (8b) was then obtained after purification by HPLC.

The structural analysis of the product obtained was in accordance with that of the expected product:

ESI: m/z=797.5 [M+H]$^+$/2

II) Photophysical Properties of the Compound of Formula (8b)

Figure 5:
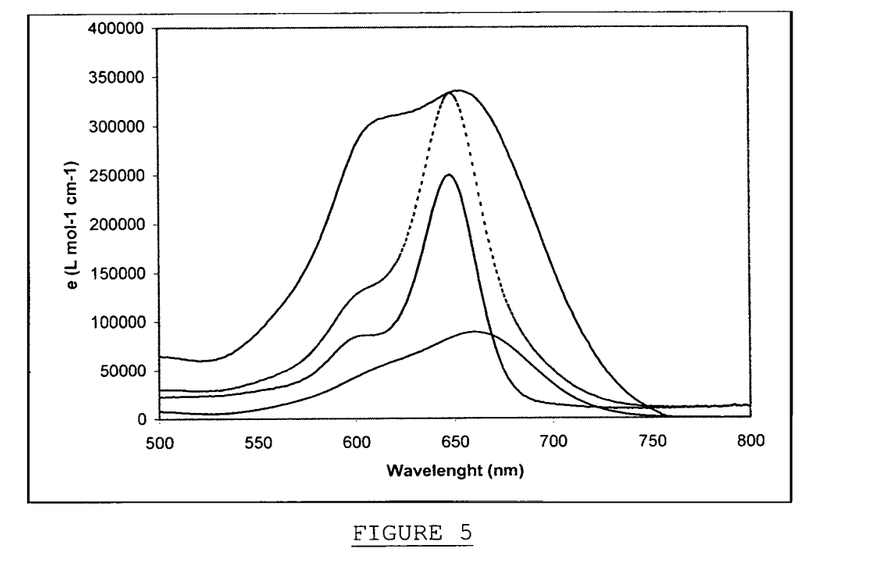
FIG. 5 represents the absorption spectrum of the compound of formula (8b) in solution at 0.99 μM in PBS (highest continuous curve), compared with those of QSY® 21 alone in solution at 0.99 μM in methanol (lowest continuous curve), of Cy5 alone in solution at 0.99 μM in PBS (intermediate continuous curve) and of the mixture of QSY® 21 at 0.99 μM/Cy5 at 0.99 μM in solution in PBS (dashed curve). In this figure, the absorption e (in L mol$^{-1}$ cm$^{-1}$) is expressed as a function of the wavelength (nm)

FIG. 5 represents the absorption spectrum of the compound of formula (8b) in solution at 0.99 μM in PBS (highest continuous curve), compared with those of QSY® 21 alone in solution at 0.99 μM in methanol (lowest continuous curve), of Cy5 alone in solution at 0.99 μM in PBS (intermediate continuous curve) and of the mixture QSY® 21 at 3.5 μM/Cy5 at 3.5 μM in solution in PBS (dashed curve). In this figure, the absorption e (in L mol-1 cm$^{-1}$) is expressed as a function of the wavelength (nm).

These spectra confirm that there has indeed been grafting both of the Cy5 fluorophore and of the QSY® 21 fluorescence inhibitor.

Figure 6:
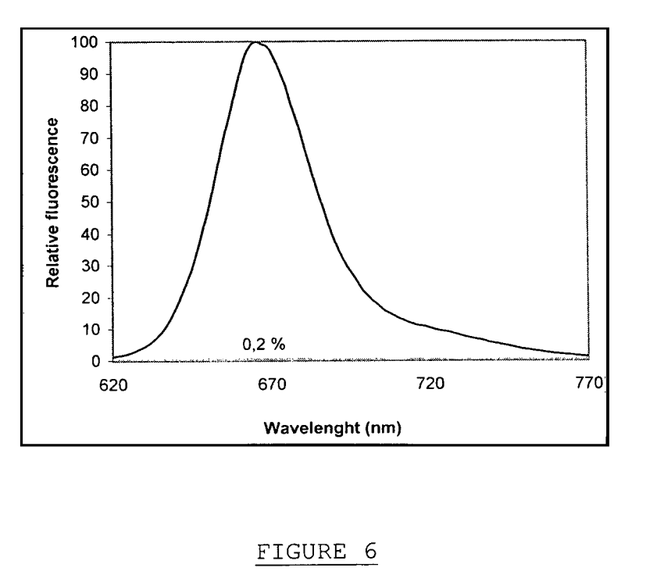
FIG. 6 represents the emission spectra (after excitation at 600 nm) of the compound of formula (8b) (nonexistent curve) compared with Cy5 (top curve). In this figure, the fluorescence (arbitrary units) is expressed as a function of the wavelength (nm).

The emission spectra of the compound of formula (8b) and of the Cy5, after excitation at a wavelength of 600 nm, were also measured and are given in the attached FIG. 6, in which the relative fluorescence (arbitrary units) is expressed as a function of the wavelength (in nm). In this figure, the top curve represents the fluorescence observed for Cy5, no fluorescence being observed for the compound of formula (8b). The proximity of the fluorescence inhibitor clearly produces inhibition of the fluorescence of the fluorophore (99.8% inhibition).

The invention claimed is:

1. A fluorescent enzymatic substrate comprising:
    a backbone S of saccharide nature comprising at least one saccharide unit selected from the group consisting of monosaccharides, oligosaccharides having from 2 to 9 saccharide units, and polysaccharides having at least 10 saccharide units;
    $B_1$ and $B_2$ connected to the backbone S, $B_1$ and $B_2$ being identical or different, each $B_1$ and $B_2$ representing a spacer arm comprising a linear or branched, saturated or unsaturated hydrocarbon-based chain optionally substituted, interrupted and/or ending with one or more heteroatoms selected from the group consisting of N, O and S, and/or with one or more groups selected from the group consisting of $C_1$-$C_4$ alkyl, $C_1$-$C_4$ alkoxy and aryl radicals or with one or more functions selected from the group consisting of ether, ester, amide, carbonyl, carbamate, urea, thiourea and disulfide functions, wherein $B_1$ and $B_2$ are present or absent, independently of one another;
    a fluorophore group $F_1$; and
    an inhibitor $I_1$ of the fluorescence of $F_1$;
    wherein
    the fluorophore group $F_1$ and the inhibitor $I_1$ do not comprise a saccharide structure;
    the backbone S comprises at least one monosaccharide comprising $F_1$ and $I_1$ grafted thereto, either directly or by the spacer arms $B_1$ and $B_2$, respectively, when at least one $B_1$ and $B_2$ is present;
    one of the groups $F_1$ and $I_1$ is grafted in the anomeric position 1 of said monosaccharide, the anomeric bond being without distinction in the α- or β-position, the other group $F_1$ or $I_1$ occupying any free position of the same saccharide unit; and
    no phosphate chain, saccharide unit or nitrogenous base intercalates between the saccharide unit of the backbone S bearing the groups $F_1$ and $I_1$, and said groups $F_1$ and $I_1$.

2. The substrate as claimed in claim 1, wherein the saccharide unit of the backbone S of the substrate is at least one selected from the group consisting of galactose, mannose, idose, talose, rhamnose, glucose, ribose, fucose and their amino or acid derivatives.

3. The substrate as claimed in claim 2, wherein the amino and acid derivatives of the saccharide unit are at least one selected from the group consisting of galactosamine, glucosamine, lactosamine, glucuronic acid, iduronic acid, and sialic acid.

4. The substrate as claimed in claim 2, wherein the saccharide unit of the backbone S of the substrate is at least one selected from the group consisting of glucosamine, galactose and glucuronic acid.

5. The substrate as claimed in claim 1, wherein the backbone S is at least one oligosaccharide comprising from 4 to 9 saccharide units.

6. The substrate as claimed in claim 1, wherein at least one of the groups $F_1$ and $I_1$ is directly linked to the monosaccharide at the end of the backbone S, and the group $F_1$ or $I_1$ which is in the anomeric position 1 of the monosaccharide is linked to the monosaccharide by a covalent bond involving at least one atom X selected from the group consisting of oxygen, carbon, sulfur and nitrogen atoms.

7. The substrate as claimed in claim 1, wherein the free positions of the saccharide unit of the backbone S, which comprise neither the fluorophore group $F_1$ nor the inhibitor group $I_1$, and which are not involved in a glycosidic bond, can without distinction be unsubstituted (—H or —OH) or substituted with an amine function or with a group resulting from the interaction of a hydroxyl function or of an amine function with a protective group.

8. The substrate as claimed in claim 1, wherein the fluorophore group is at least one selected from the group consisting of fluorescein and its derivatives; fluorescent dyes that absorb and emit in the near infrared range; Cy5 (n=2) and Cy7 (n=3); 7-hydroxy-9H-(1,3-dichloro-9,9-dimethylacridin-2-one); rhodamine and its derivatives; fluorescent dyes comprising reactive amines; porphyrins; cyanins; oxazines and fluorescent nanoparticles.

9. The substrate as claimed in claim 8, wherein the fluorophore group is at least one fluorophore group that absorbs and emits in the near infrared range.

10. The substrate as claimed in claim 9, wherein the group $F_1$ is 7-hydroxy-9H-(1,3-dichloro-9,9-dimethylacridin-2-one).

11. The substrate as claimed in claim 1, wherein the fluorophore group $F_1$ is further functionalized with one or more groups selected from the group consisting of lipophilic chains, phospholipids and peptides.

12. The substrate as claimed in claim 1, wherein the group $I_1$ is a fluorescent group whose fluorescence inhibits or absorbs fluorescence of the group $F_1$.

13. The fluorescent substrate as claimed in claim 12, wherein the group $I_1$ is a fluorescent group which is different from the group $F_1$ and which absorbs the fluorescence of the group $F_1$ by fluorescence resonance energy transfer.

14. A method for detecting an enzymatic activity in vitro comprising applying at least one enzymatic substrate as defined in claim 1, as a fluorescent reagent, to a sample.

15. A method for preparing a diagnostic reagent for in vivo functional imaging comprising applying to a sample at least one enzymatic substrate as defined in claim 1, wherein the fluorophore group $F_1$ is at least one group that absorbs and emits in the near infrared range.

16. The method as claimed in claim 15, wherein said enzymatic substrate is applied to the sample for imaging the expression of the *E. coli* LacZ and gusA reporter genes by fluorescence.

17. A diagnostic reagent comprising at least one solution comprising water or a mixture of water and at least one organic solvent, and at least one enzymatic substrate as defined in claim 1.

18. The reagent as claimed in claim 17, wherein said reagent is an in vivo diagnostic reagent and the enzymatic substrate comprises at least one fluorophore group $F_1$ that absorbs and emits in the near infrared range.

19. The reagent as claimed in claim 17, wherein the concentration of the enzymatic substrate is between 1 μM and 1 mM.

20. The substrate as claimed in claim 1, wherein $B_1$ and $B_2$ do not comprise a saccharide unit.

21. A fluorescent enzymatic substrate comprising:
a backbone S of saccharide nature comprising at least one saccharide unit selected from the group consisting of monosaccharides, oligosaccharides having from 2 to 9 saccharide units, and polysaccharides having at least 10 saccharide units;
$B_1$ and $B_2$ connected to the backbone S, $B_1$ and $B_2$ being identical or different, each $B_1$ and $B_2$ representing a spacer arm comprising a linear or branched, saturated or unsaturated hydrocarbon-based chain optionally substituted, interrupted and/or ending with one or more heteroatoms selected from the group consisting of N, O and S, and/or with one or more groups selected from the group consisting of $C_1$-$C_4$ alkyl, $C_1$-$C_4$ alkoxy and aryl radicals or with one or more functions selected from the group consisting of ether, ester, amide, carbonyl, carbamate, urea, thiourea and disulfide functions, wherein $B_1$ and $B_2$ do not comprise a saccharide unit;
a fluorophore group $F_1$; and
an inhibitor $I_1$ of the fluorescence of $F_1$;
wherein
the backbone S comprises at least one monosaccharide comprising $F_1$ and $I_1$ grafted thereto by the spacer arms $B_1$ and $B_2$, respectively;
one of the groups $F_1$ and $I_1$ is grafted in the anomeric position 1 of said monosaccharide, the anomeric bond being without distinction in the α- or β-position, the other group $F_1$ or $I_1$ occupying any free position of the same saccharide unit; and
no phosphate chain, saccharide unit or nitrogenous base intercalates between the saccharide unit of the backbone S bearing the groups $F_1$ and $I_1$, and said groups $F_1$ and $I_1$.

22. The substrate as claimed in claim 21, wherein the fluorophore group absorbs and emits at wavelengths of between 640 and 900 nm such that the substrate is capable of detecting an enzymatic activity in vivo by fluorescence at the wavelengths.

* * * * *